United States Patent [19]

Sitte

[11] Patent Number: 4,578,963
[45] Date of Patent: Apr. 1, 1986

[54] APPARATUS FOR THE CRYOFIXATION OF SPECIMENS

[75] Inventor: Hellmuth Sitte, Siefeld/Triol, Austria

[73] Assignee: C. Reichert Optische Werke, AG, Vienna, Austria

[21] Appl. No.: 729,762

[22] Filed: May 2, 1985

[30] Foreign Application Priority Data

May 7, 1984 [DE] Fed. Rep. of Germany ....... 3416790

[51] Int. Cl.⁴ ............................................. F25B 19/00
[52] U.S. Cl. ..................................... 62/514 R; 62/383
[58] Field of Search .................. 62/49, 514 R, 383, 78

[56] References Cited

U.S. PATENT DOCUMENTS 3,479,833 11/1969 Waldin .................................. 62/374
4,302,950 12/1981 Sitte .................................. 62/514 R Primary Examiner—Ronald C. Capossela
Attorney, Agent, or Firm—Alan H. Spencer; S. Raines

[57] ABSTRACT

Apparatus for the cryofixation of specimens, comprises a tank adapted to contain a cold gaseous medium having an upper boundary with an atmosphere external to the tank, and cooling means having an upper surface, said cooling means being disposed within the tank. The upper surface is movable between a lower level and an upper level which is below the upper boundary. The upper surface is maintained at the upper level for a period sufficient to permit the application of a specimen to the upper surface, and is then lowered to the lower level.

15 Claims, 9 Drawing Figures

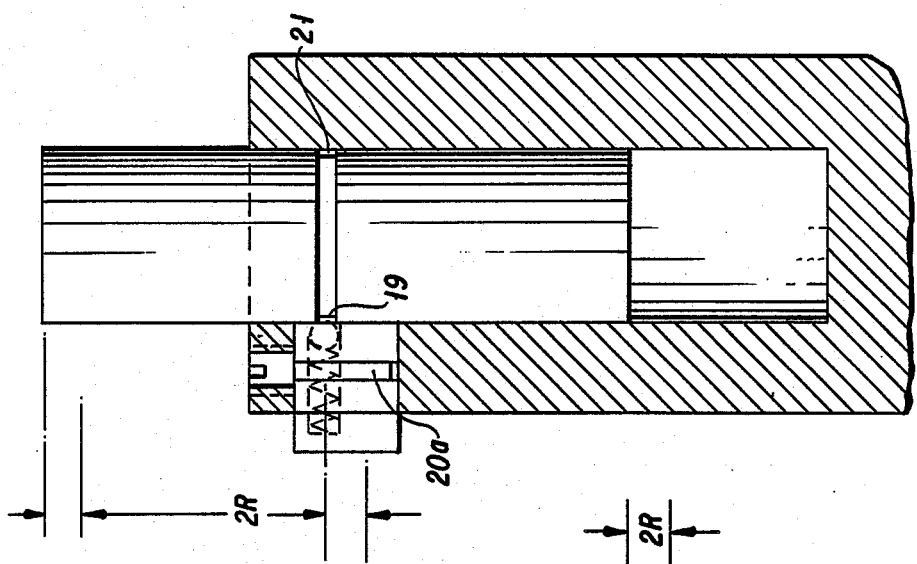
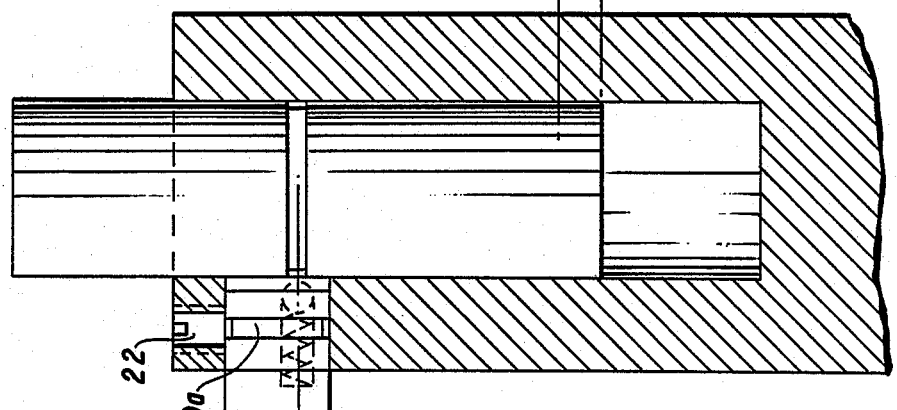
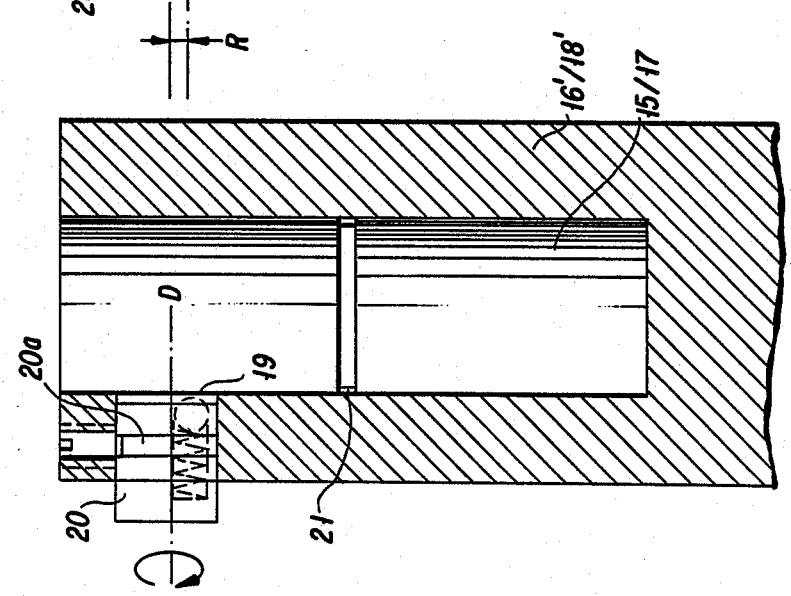

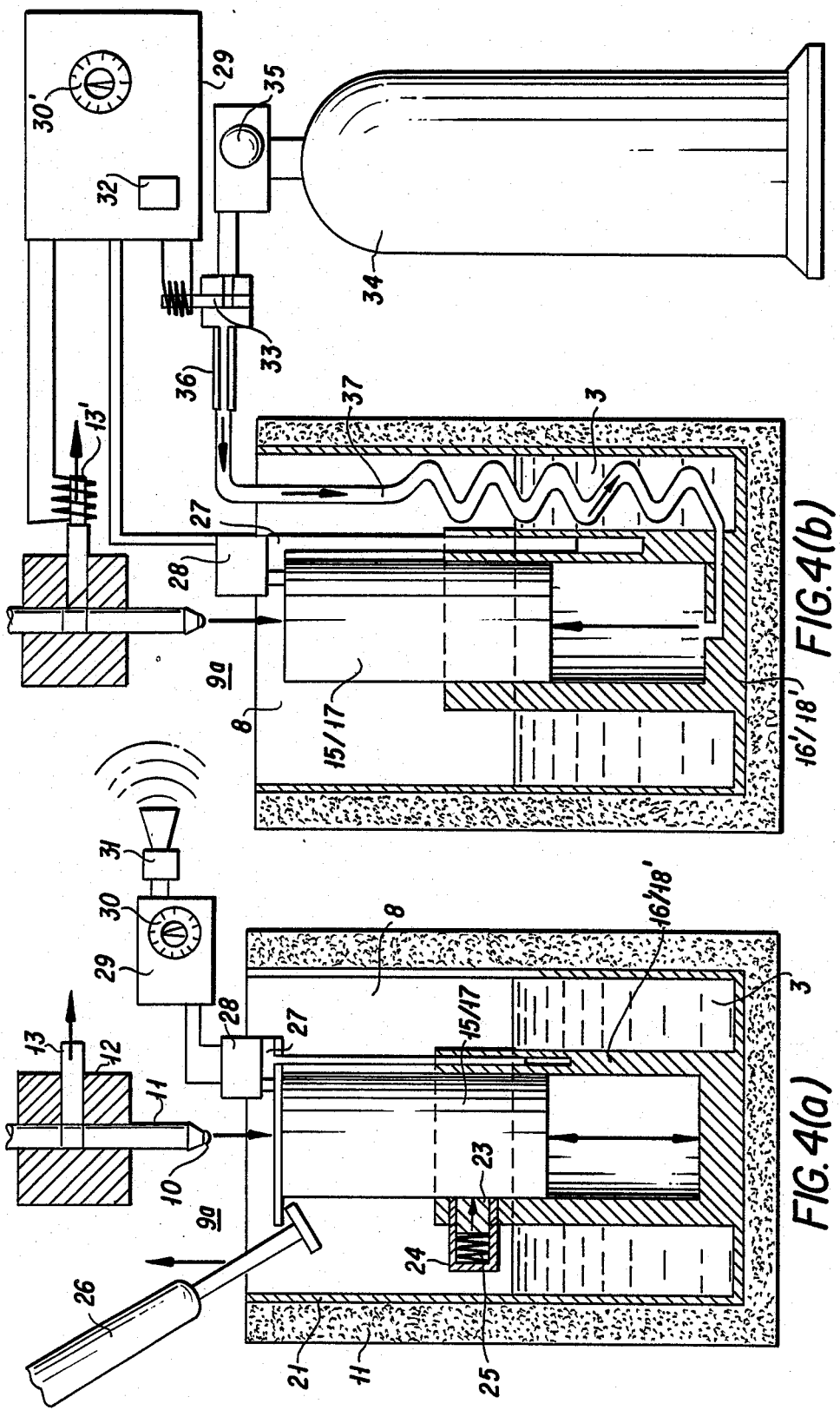

APPARATUS FOR THE CRYOFIXATION OF SPECIMENS

BACKGROUND OF THE INVENTION

This invention relates to apparatus for the cryofixation of specimens, particularly natural specimens.

The cryofixation of natural specimens is commonly carried out by immersion cryofixation, or by metal mirror surface cryofixation (which is also known as slammer system cryofixation). In immersion cryofixation, the specimen is cooled rapidly from room temperature or from body temperature to a temperature below $-100°$ C. by introducing it into a cooling bath. In metal mirror surface cryofixation, the specimen is struck against a highly polished metal surface to effect the necessary cooling.

In carrying out these processes it would be desirable, particularly in the case of sensitive biological or medical specimens or technical specimens with a similarly high water or fluid content, which have not been pretreated by a chemical fixation and/or anti-freeze agent (such as sugar or glycerine), to achieve a sharp transition from room temperature or body temperature to the fixation temperature. However, this is impossible in practice, because the surface level of the refrigerant liquid or of the metal mirror surface must not be allowed to come into contact with the room atmosphere, but must always remain covered by a cold inert gas such as gaseous nitrogen. Otherwise, water vapour, $CO_2$ and $O_2$ would immediately be deposited upon the low temperature liquid (normally at $-160°$ C. or below) or on the deeply cooled metal mirror surface.

Frost precipitations of this type would immediately render the metal mirror surface unserviceable. And in immersion cryofixation such deposits would abruptly alter the composition of the liquid cryogen, rendering it unsuitable for cryofixation. In the case of liquid propane, which is commonly used for immersion cryofixation, there is also the possibility of an $O_2$ accumulation which leads to an acute danger of explosion.

In order to eliminate these risks, it is not sufficient merely toi maintain a thin covering layer of dry cold gaseous nitrogen over the liquid surface or the metal mirror surface. It is in addition also necessary to dimension the depth of this protective layer so that a covering layer of gaseous nitrogen is always maintained, even when air currents are present in the room. Adequate long-term security can only be ensured in such a case if the liquid surface level or the metal mirror surface is located at approximately 15 to 20 mm below the boundary layer which the cold dry gaseous nitrogen forms with the external room atmosphere. During the injection of the specimen into the refrigerant medium or on to the metal mirror surface, it must then first of all penetrate this protective layer of 15 to 20 mm cold gaseous nitrogen before it enters the refrigerant medium itself or strikes the metal mirror surface. During this operation it is impossible to prevent unnatural modification of the surface layer of the specimen that is of interest, because due to its low thermal capacity and poor thermal conductivity the gaseous nitrogen permits deleterious cooling but does not enable rapid stabilisation to be achieved by the freezing process.

SUMMARY OF THE INVENTION

It is an object of the invention to overcome the disadvantages set out above, and to provide apparatus which reduces the transfer of natural specimens through cold gaseous nitrogen to a minimum without incurring the risk of a detrimental accumulation of $H_2O$, $CO_2$ and $O_2$ from the external room atmosphere on the liquid surface or on the metal mirror surface.

According to the present invention there is provided apparatus for the cryofixation of specimens comprising a tank adapted to contain a cold gaseous medium having an upper boundary with an atmosphere external to the tank, cooling means having an upper surface, said cooling means being disposed within the tank, wherein said upper surface is movable between a lower level and an upper level below said upper boundary, and said upper surface can be maintained at the upper level for a period sufficient to permit the application of a specimen to the upper surface.

The positioning of the upper level varies according to the conditions in the external atmosphere. The upper level should be as close to the upper boundary as the air currents in the surrounding external atmosphere permit. In normal circumstances, this distance may be not more than about 5 mm, and in particularly advantageous conditions this distance may be 3 mm or less.

In one embodiment the cooling means may comprise a liquid refrigerant medium having a liquid surface corresponding to said upper layer. The liquid refrigerant medium may be contained by a reservoir.

In another embodiment the cooling means may comprise a member having a metal mirror surface corresponding to said upper layer.

The invention thereby provides that the depth of the protective gas atmosphere, such as gaseous nitrogen, is reduced, by raising the level of the liquid surface or of the metal mirror surface, as far as possible without risking frost precipitation, immediately before the injection of the specimen into the refrigerant medium or onto the metal mirror surface. The liquid surface or metal mirror surface can be lowered again immediately after the injection.

At the lower level of the cooling means, where the respective surfaces rest during stand-by operation, which comprises well over 99% of the operating time of such a system, any risk of an undesirable level of gas accumulation on the refrigerant medium or on the metal mirror surface can be reliably eliminated.

In a preferred embodiment of the invention, wherein the refrigerant medium or the metal mirror surface is raised manually, detent means such as a ball catch device or other known mechanically equivalent element determines the upper level. In a similar manner, movement beyond the upper level may be limited by stop means, and a permanently engaged mechanical brake may hold the liquid medium reservoir or metal mirror surface at the upper level.

When the refrigerant medium or metal mirror surface is raised manually, there is a danger of the cooling means remaining inadvertently in the raised position after cryofixation is completed, which prevents further continuation of the work. Accordingly, an alarm may be provided to generate an alarm signal to remind the operator that the cooling means is still at the upper level. A trigger may be provided to actuate the alarm when the trigger is in contact with the cooling means, the trigger being disposed so that it is in contact with the cooling means when the cooling means is in the upper position. A "dead man's" control of a known kind may be provided to actuate the trigger at a specific prescribed or preselectable period after the cooling means contacts the trigger. The operator is thus able to restore the cooling means back into the stand-by position in good time.

In accordance with another advantageous feature of the invention, an operative connection may be established between the initiation of the injection process and the raising of the liquid surface or of the metal mirror surface. Displacement means may be provided for automatically raising and lowering the cooling means and a start control may be provided for actuating the displacement means. After operation of the start control, the apparatus first of all raises the liquid surface or metal mirror surface and, through the operative connection, initiates the injection of the specimen only when the raising stroke has been completed. After completion of the injection step the apparatus returns the liquid surface or metal mirror surface back to its initial stand-by position. Such automated apparatus may be controlled by a wide variety of electro-mechanical means. In a particularly preferred embodiment the apparatus includes pneumatic means for raising and lowering the cooling means and stop means for limiting the raising and lowering movements effected thereby, the pneumatic means being actuated by pre-cooled compressed gas, such as gaseous nitrogen. Control means for the apparatus may include a solenoid valve at an adjustable limit.

The upper level may be preselectable within a predetermined range and may be reproducible in the preselected position.

BRIEF DESCRIPTION OF THE DRAWINGS

Reference is now made to the accompanying drawings, in which:

FIGS. 3a, 3b and 3c are detailed views showing in diagrammatic cross-section stages in the operation of a further development of the apparatus of FIGS. 2a and 2b; and FIGS. 4a and 4b show in diagrammatic cross-section further embodiments of the apparatus according to the invention.

DESCRIPTION OF THE PREFERRED EMBODIMENTS

Figure 1A:
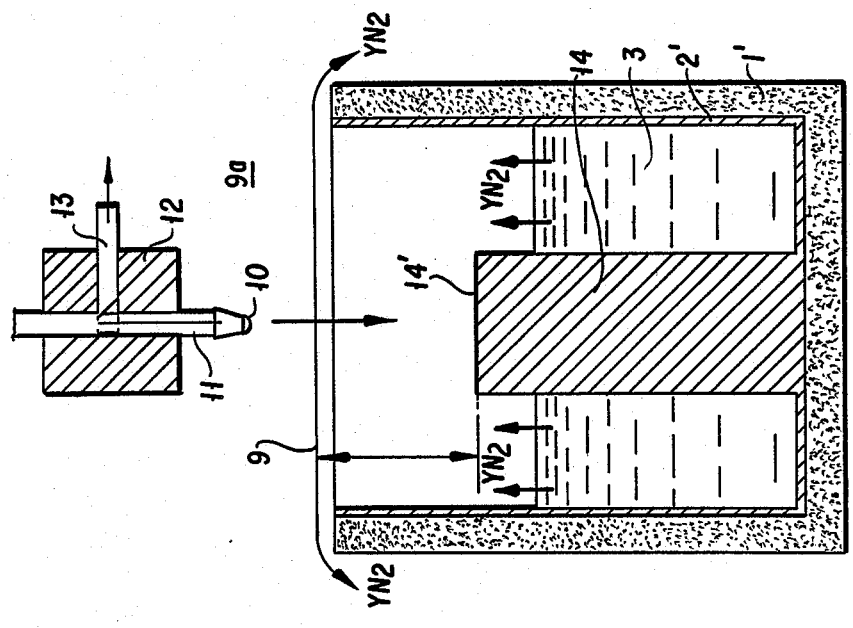
FIGS. 1a and 1b show respectively in diagrammatic cross-section prior art apparatus for cryofixation by immersion and on a metal mirror surface.
Figure 1B:
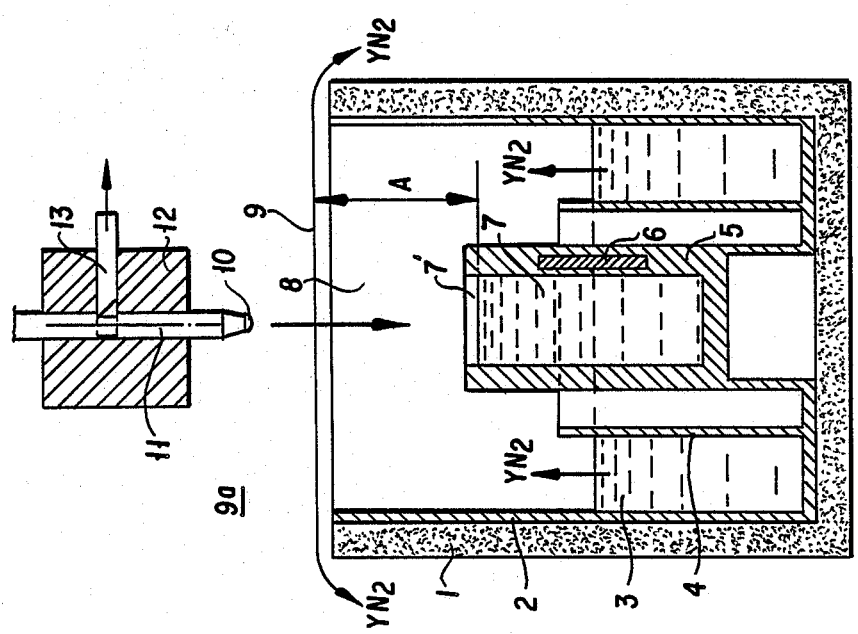

The apparatus illustrated in cross-section in FIGS. 1a and 1b, in simplified form and purely diagrammatically, correspond to the prior art. The cryogen is liquid nitrogen ($LN_2$) designated 3 and is contained in a tank 2 surrounded by thermal insulation 1.

In FIG. 1, which illustrates apparatus for immersion cryofixation, a reservoir 5 for a liquid refrigerant medium 7 is shown in a stand-by position.

Any direct contact between the liquid nitrogen 3 and the surface of the reservoir 5 in the stand-by operation is prevented by a sleeve 4, so that by means of a resistance heating element 6 the temperature of the refrigerant medium 7 can be thermostatically maintained at values which lie above the boiling point of liquid nitrogen ($-196°$ C.). Cold dry gaseous nitrogen ($GN_2$) fumes off steadily from the liquid nitrogen 3 and forms a cold pool 8 in the tank 2 with a clearly defined upper boundary layer 9 with an external atmosphere 9a. The boundary layer 9 of the gaseous nitrogen pool 8 is defined by a temperature gradient which may amount to over 100° C. in a vertical distance of approximately 1 mm. The surface of the gaseous nitrogen pool 8, which is defined by this temperature gradient, lies just above the upper rim of the tank 2, and the arrows indicate that the cold gaseous nitrogen evolved steadily from the liquid nitrogen flows away over the upper rim.

A trigger 13 is provided on a guide element 12, and a specimen 10 is attached to an injector 11 disposed within the guide element 12. After actuation of the trigger 13 the specimen 10 is injected in the injector 11 through the boundary layer 9 into the cold gaseous nitrogen 8 before it strikes an upper surface 7' of the refrigerant medium 7.

The distance between the upper boundary layer 9 and the upper surface 7' is designated A. Within the distance A between the upper boundary 9 and the surface level 7', the specimen 10 passes through cold gaseous nitrogen which causes superficial cooling of the specimen 10 without freezing it rapidly, because the specific heat and density of the gaseous nitrogen 8 is quite insufficient for rapid vitrification. Moreover, the specimen 10 may in part suffer substantial thermal damage by pre-cooling before final vitrification, particularly in the surface layers which are best vitrified by a rapid cryofixation. Thus, upon entering the refrigerant medium 7, the specimen 10 is already in an unnaturally altered condition which no longer corresponds to the natural state before injection.

Similar considerations apply to metal mirror cryofixation, for which prior art apparatus is illustrated in simplified form in FIG. 1b. Cooling means comprises a member in the form of a block 14 of suitable metal such as 99.999% copper or silver; copper is preferred when the cyrogen is liquid nitrogen, and silver is preferred when the cryogen is liquid helium. The block 14 is mounted in a tank 2', which is surrounded by thermal insulation 1' and filled with liquid nitrogen 3 as cryogen. A plane upper surface 14' of the block 14 is polished to a high gloss and forms the metal mirror surface to which the specimen 10 is applied, in the manner already described, after actuation of the trigger 13, the application generally being effected at high speed in a conventional manner. In the apparatus for metal mirror surface cryofixation, as in the apparatus for immerison cryofixation shown in FIG. 1a, the specimen 10 first of all passes through the boundary layer 9, enters the cold gaseous nitrogen pool 8 and travels the distance A in the cold gas before it strikes the metal mirror surface 14' and is finally vitrified.

In each case it is impossible to raise the liquid surface level 7' or the metal mirror surface 14' to the vertical level of the upper boundary layer 9 between the cold gaseous nitrogen 8 and the external room atmosphere 9a, because $H_2O$, $CO_2$ and $O_2$ would then immediately accumulate on the liquid surface 7' or on the metal mirror surface 14'. This would cause the composition of the refrigerant medium 7 to be rapidly altered, or an interrupting frost layer to be formed on the metal mirror surface 14'. Both of these phenomena would preclude any further use of the refrigerant medium 7 or of the metal mirror surface 14'. Where liquid propane is used as the refrigerant medium 7 for immersion cryofixation, the accumulation of $O_2$ by the refrigerant medium additionally creates an acute risk of explosion, which it is important to prevent. It is impossible to avoid this risk providing apparatus in which the liquid surface level 7' or the metal mirror surface 14' is at a level which lies immediately below the boundary layer 9, because the boundary layer 9 is continually making slight unpredictable movements caused by air currents in the external atmosphere 9a and by the boiling process at the surface of the liquid nitrogen 3; thus the surfaces 7' and 14' would be repeatedly exposed to the external atmosphere 9a for short periods.

The disadvantages of the prior art apparatus, detailed above with reference to FIGS. 1a and 1b, can be avoided in a simple manner by utilisation of apparatus according to the present invention. This is shown in FIGS. 2a and 2b, which illustrate the apparatus according to the prior art modified in accordance with the invention.

Figure 2B:
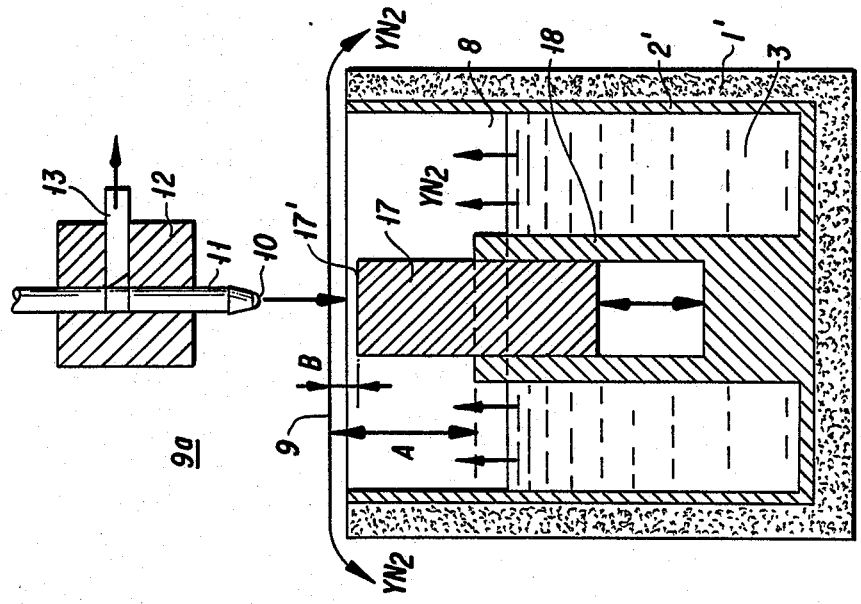
FIGS. 2a and 2b show respectively indiagrammatic cross-section corresponding apparatus in accordance with the invention for cryofixation by immersion and on a metal mirror surface.
Figure 2A:
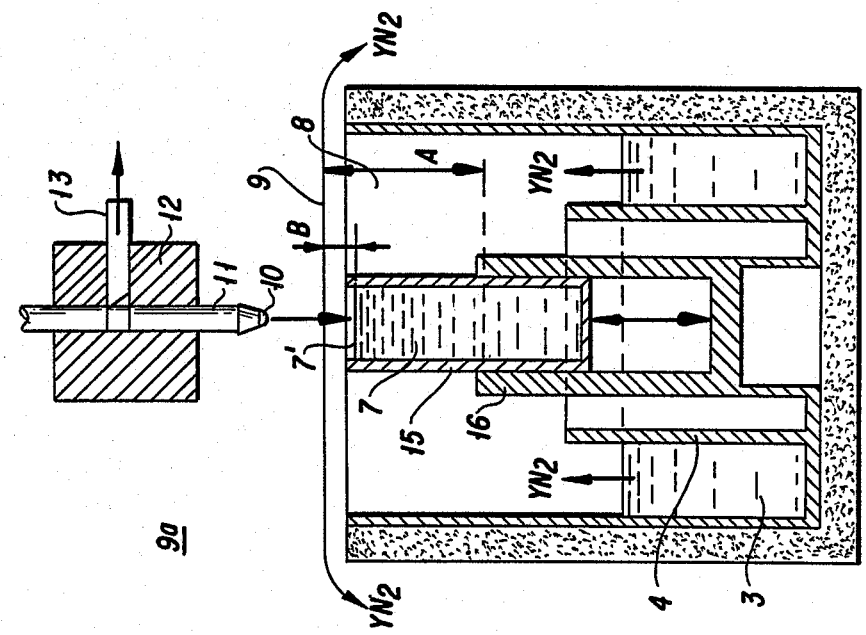

Apparatus for immersion cryofixation is illustrated in FIG. 2a; the refrigerant medium 7 is contained in a tubular reservoir 15 which is in turn accommodated in a metal receptacle 16 which otherwise generally corresponds to the metal reservoir 5 shown in FIG. 1a. The surface level 7' of the liquid 7 is raised by movement of the reservoir 15 relative to the stationary receptacle 16.

Apparatus for metal mirror surface cryofixation is illustrated in FIG. 2b. A metal block 17 with a metal mirror surface 17' which is arranged similarly in a receptacle 18 and can be raised by movement of the block 17 relative to the stationary receptacle 18.

The liquid surface level 7' or the metal mirror surface 17' is movable between a lower level and an upper level. The lower level corresponds to the stand-by position and is shown by a dashed line 40 in FIGS. 2a and 2b. The surface 7' or 17' is raised immediately before the injection of the specimen 10 to the extent that only a minimal distance B remains between the surface 7' or 17' and the boundary layer 9. The distance B is selected according to available experience based on the dimensions and design of the apparatus to provide with sufficient surety that the accumulation of $H_2O$, $CO_2$ and $O_2$ on the surface 7' or 17' does not take place to a detrimental extent in the short period concerned. The duration of the short period may typically be in the region of 1 to 3 seconds, and should be as small as possible.

Immediately after injection of the specimen 10 into the refrigerant medium 7 or onto the metal mirror surface 17', the surfaces 7' or 17' can be lowered again. Because the injection process is concluded within a very short time, the apparatus is, for over 99% of its operating time, in the stand-by position which is at the distance A from the upper boundary 9 and which is selected so that any accumulation of $H_2O$, $CO_2$ or $O_2$ is prevented.

Various further modifications of apparatus according to the invention are possible, as will be described below. Because of the equivalence in these cases between the raising of the reservoir 15 filled with the liquid refrigerant medium 7 and the raising of the metal block 17 having the mirror surface 17', the following description of the apparatus illustrated in FIGS. 3 and 4 refers simply to the respective elements as 15/17, 7'/17' and 16'/18'. In order to avoid undue repetition, neither of the two systems simultaneously designated in this manner is identified separately.

In the advantageous further modification of the apparatus shown in FIGS. 3a, 3b and 3c, detent means in the form of a spring-loaded ball catch, comprising ball 19 in a support 20, (or an equivalent element such as a spring-loaded pin) is provided. An annular groove 21 or an equivalent depression in the elements 15/17 is provided so that when the surfaces 7'/17' are at the upper level, the ball 19 engages the groove 21. The detent means thereby determines the location of the elements 15/17 at the upper level. The vertical level of ball 19 may be either fixed or adjustable. One example of such an arrangement is shown in FIGS. 3a, 3b and 3c, in which the support 20 is rotatable about a horizontal rotary axis DD in the elements 16'/18'. If the ball 19 is positioned eccentrically relative to the axis DD, by a radius R, a vertical adjustment over a distance of 2R can be obtained by rotating the ball catch 19/20. The preselected position may be fixed by, for example, a locking screw 22 engaging an annular groove 20a in the support 20. FIG. 3a shows the embodiment in the stand-by position with the surfaces 7'/17' at the lower level. FIG. 3b and FIG. 3c show the same apparatus in the raised position with the surfaces 7'/17' at the upper level ready for injection and cryofixation; FIG. 3b illustrating the lowest selectable position of the upper level and FIG. 3c illustrates the highest selectable position of the upper level.

FIG. 4a shows a further embodiment of the apparatus. In place of the ball catch 19/20, a friction brake is provided on the receptacle 16'/18'. In the simplest case the brake comprises a friction brake shoe 23 in a sleeve 24, and a spring 25 is provided to urge the shoe 23 against the element 15/17, thereby maintaining that element securely at any desired vertical level. In the simplest case, the element 15/17 is raised and lowered manually by the use of a suitable tool 26. Upward movement beyond the upper level may be limited by stop means in the form of an adjustable stop 27 carried by the receptacle 16'/18'.

A trigger in the form of a contact element 28 may be connected to the adjustable stop 22 in a known manner. The contact element 28 is disposed so that when the surfaces 7'/17' reach the upper level the element 28 generates a signal which is transmitted to an electronic system 29. The electronic system 29 generates a signal to actuate an alarm 31. For example, the alarm 31 may comprise a loudspeaker which generates an alarm signal in the form of a noise. The electronic system 29 includes a delay circuit (known as a dead-man's circuit) and generates the signal to actuate the alarm 31 if the contact 28 has not been reopened by lowering the elements 15/17 before the expiry of a pre-set period. This period may be fixed, or it may be preselectable by means of an adjusting knob 30. An alarm device of this type is particularly advantageous when liquid propane is used as the cooling medium 7, in which case an accumulation of $0_2$ would create a substantial explosion risk.

In another further modification of the apparatus an operative connection may be established in a manner known per se such that after actuation of an electrical or mechanical switch element, the element 15/17 is raised, and after the upward movement is completed the trigger 13' is actuated by a signal from the contact element 28 and injection of the specimen is thereby initiated. The lowering stroke can be actuated by means of a delay circuit in the electronic system 29'/30' (FIG. 4b). Apparatus controlled in this manner may be constructed in a wide variety of ways using known mechanical, electrical or electromechanical components to be actuated by the electronic system 29'/30' in the course of the operating cycle.

Of the many possible alternatives, one embodiment of such apparatus utilising a pneumatic system for raising and lowering the cooling means is described by way of example with reference to FIG. 4b. In this case an electrical signal from a start control button 32 causes a solenoid valve 33 to open, and compressed gaseous nitrogen is thereby released from a pressure cylinder 34 through a reducing valve 35 and passes by way of a reduction piece 36 slowly into tubular pipework 37. The gaseous nitrogen is first pre-cooled in the pipework 37 by the liquid nitrogen 3 in the tank 1' and then raises the element 15/17, which acts as a piston, until it reaches stop 27. The element 15/17 then remains stationary under sustained pressure with the surfaces 7'/17' at the upper level. Injection of the specimen 10 can now be initiated, either indirectly or directly by means of the contact 28, by retraction of electormagnetic trigger 13'. After injection is completed, a delay switch (not shown) may close the solenoid valve 33 and the elements 15/17 may be returned to the lowered stand-by position by the slow escape of gaseous nitrogen to the gaseous nitrogen pool 8 from the cavity formed by the piston element 15/17 and the cylinder constituted by the receptacle element 16'/18'. Such lowering may be accelerated by use of a compression or tension spring (not shown) acting on the element 15/17.

The above described exemplary embodiments and structural combinations may be varied within the scope of the invention without departing from the essential character of the apparatus. Thus, it is possible to combine mechanical, electronic, electromechanical or pneumatic elements in different ways in apparatus within the scope of the present invention.

I claim:

1. Apparatus for cryofixation of specimens comprising,
    a cryogen container, said container having sidewalls to retain a liquid cryogen and a gaseous barrier layer of the cryogen covering the liquid cryogen,
    cryofixation means movably mounted in said container for cryofixation of a specimen, said cryofixation means including a surface,
    positioning means for moving said surface between first and second positions, said first position being located a substantial distance from the top of said barrier layer and said second position being located proximate the top of said barrier layer,
    whereby said cryofixation means is protected from the ambient atmosphere by said barrier layer and effectively cooled by said cryogen when said surface is in said first position, while rapid contact of a specimen with said surface does not significantly disturb said barrier layer and the specimen is not prematurely cooled by said barrier layer, when said surface is in said second position.

2. Apparatus according to claim 1, wherein said second position is not more than about 5 mm below the top of said barrier layer.

3. Apparatus according to claim 1, in which the cryofixation means includes a liquid refrigerant having a surface.

4. Apparatus according to claim 3, further comprising a removable reservoir for the liquid refrigerant medium.

5. Apparatus according to claim 4, further comprising a braking element adapted to maintain the cryofixation liquid at the second position, and stop means adapted to prevent upward movement of the surface beyond the second position.

6. Apparatus according to claim 5, in which the location of the second position is adjustable.

7. Apparatus according to claim 4, further including an alarm, and a trigger adapted to actuate the alarm when in contact with the reservoir, the alarm being adapted to create an alarm signal after the elapse of a pre-selected period following actuation by the trigger, said trigger being disposed such that it is in contact with the reservoir when the surface is at the second position.

8. Apparatus according to claim 1, in which said surface is a metal surface.

9. Apparatus according to claim 8 further including a braking element adapted to maintain said metal surface at the second position, and stop means adapted to prevent upward movement of the metal surface beyond the second position.

10. Apparatus according to claim 8 in which the location of the second position is adjustable.

11. Apparatus according to claim 8 further comprising an alarm and a trigger adapted to actuate the alarm when in contact with said cryofixation means, the alarm being adapted to create an alarm signal after the elapse of a pre-selected period following actuation by the trigger, said trigger being disposed such that it is in contact with the cryofixation means when the metal surface is at the second position.

12. Apparatus according to claim 1 further comprising detent means adapted to determine the location of the second position.

13. Apparatus according to claim 1 wherein said positioning means includes displacement means for raising and lowering said surface, and a control, said displacement means being actuatable in response to actuation of the control.

14. Apparatus according to claim 1 wherein said positioning means includes pneumatic displacement means for raising and lowering the metal surface, and stop means for determining the location of the first and second positions.

15. Apparatus according to claim 14 wherein said pneumatic displacement means uses gaseous cryogen.

* * * * *